United States Patent [19]
McGovern et al.

[11] Patent Number: 4,891,217
[45] Date of Patent: * Jan. 2, 1990

[54] PERSISTANT ATTRACTANTS FOR THE MEDITERRANEAN FRUIT FLY, THE METHOD OF PREPARATION AND METHOD OF USE

[75] Inventors: Terrence P. McGovern, Bowie, Md.; Roy T. Cunningham, Hilo, Hi.

[73] Assignee: The United States of America as represented by the Secretary of Agriculture, Washington, D.C.

[*] Notice: The portion of the term of this patent subsequent to Aug. 16, 2005 has been disclaimed.

[21] Appl. No.: 186,990

[22] Filed: Apr. 27, 1988

Related U.S. Application Data

[63] Continuation-in-part of Ser. No. 42,920, Apr. 27, 1987, Pat. No. 4,764,366.

[51] Int. Cl.[4] ............................................. A01N 25/00
[52] U.S. Cl. ....................................................... 424/84
[58] Field of Search .......................................... 424/84

[56] References Cited

U.S. PATENT DOCUMENTS 3,016,329  1/9162  Beroza et al. .......................... 424/84
4,152,422  5/1979  Ohinata et al. ......................... 424/84

OTHER PUBLICATIONS

M. Beroza, N. Green, and S. I. Gertler, Agricultural and Food Chemistry, "New Attractants for the Mediterranean Fruit Fly," vol. 9, No. 5, pp. 361–365 (Sep. 1961).

S. I. Gertler, L. F. Steiner, W. C. Mitchell, and W. F. Barthel, Agricultural and Food Chemistry, "Esters of 6-Methyl-3-cyclohexene-1-carboxylic Acid as Attractants for the Mediterranean Fruit Fly," vol. 6, No. 8, pp. 592–594 (Aug. 1958).

Primary Examiner—Allen J. Robinson
Attorney, Agent, or Firm—M. Howard Silverstein; Beverly K. Johnson; John D. Fado

[57] ABSTRACT

Novel attractants for the Mediterrean Fruit Fly, "Medfly," are disclosed. The attractants comprise isomeric blends of esters of iodo-trans-2-methylcyclohexanecarboxylic acid. In use, the attractants are competitive in attraction with the "standard" Medfly attractant, Trimedlure, "TML," but are much more persistent than TML.

22 Claims, No Drawings

PERSISTANT ATTRACTANTS FOR THE MEDITERRANEAN FRUIT FLY, THE METHOD OF PREPARATION AND METHOD OF USE

This application is a continuation-in-part of application Ser. No. 07/042,920, filed Apr. 27, 1987, now U.S. Pat. No. 4,764,366.

BACKGROUND OF THE INVENTION

1. Field of the Invention

This invention relates to novel attractants for the Mediterranean Fruit Fly, *Ceratitis capitata* Wiedmann, hereinafter referred to as the "Medfly." More particularly, the present invention relates to novel isomeric blends of aliphatic esters of iodo-trans-2-methylcyclohexanecarboxylic acid, the method of their preparation and the method of use thereof to attract the Medfly for prolonged periods of time.

2. Description of the Prior Art

Attacking over 250 varieties of fruits, nuts and vegetables, the Medfly is one of our most serious crop pests. Found predominately in Hawaii, Central America, and subtropical regions of the world, the Medfly has periodically invaded the mainland of the United States causing major economic losses. Consequently, there exists a great need for effective programs to control this pest.

Several attractants for the Medfly are known. Siglure (1-methylpropyl trans-6-methyl-3-cyclohexenecarboxylate) was the first synthetic lure found to have significant attraction to the Medfly. Medlure (1-methylpropyl 4(and 5)-chloro-trans-2-methylcyclohexanecarboxylate) and trimedlure (1,1-dimethylethyl 4(and 5)-chloro-trans-2-methylcyclohexanecarboxylate), hereinafter referred to as "TML," were later reported to be greatly superior as Medfly attractants.

Currently, TML is the "standard" attractant most widely used in traps for survey and detection of the Medfly. TML evaporates rapidly during hot weather thereby necessitating frequent and costly rebaiting of the traps. Further, the short residual life of TML (as well as Medlure and Siglure) mitigates against the development of an economical male-annihilation formulation of attractant plus insecticide. TML also forms crystals during cold-weather storage so that the amount of the attractant is reduced in the supernatant. Because these crystals do not readily redissolve, special storage problems can occur in larger volume programs.

SUMMARY OF THE INVENTION

An object of this invention is to provide novel attractants which are highly attractive to the Medfly for prolonged periods of time.

Another object of this invention is to provide persistent Medfly attractants which are comparable in attraction with TML but do not possess the deficiencies associated with TML.

We have accomplished the aforementioned objects by providing certain isomeric blends of lower alkyl esters of 4(and 5)-iodo-trans-2-methylcyclohexanecarboxylic acid which when applied in an amount sufficient to attract the Medfly are highly effective for prolonged periods of time. In addition to being much more persistent than TML, the esters of the invention are not prone to crystallization as is TML, and may be more facilely and economically produced than TML.

DETAILED DESCRIPTION OF THE INVENTION

In general, esters useful in the present invention are represented by the general formulae

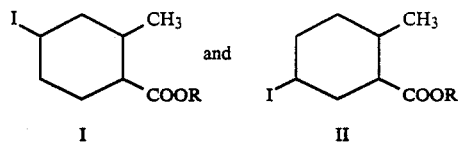

wherein —CH$_3$ and —COOR are in the trans-configuration and I is in both the equatorial and axial conformation; and wherein R is an aliphatic radical having from 1–5 carbon atoms and is selected from the group consisting of lower alkyls and fluoro-substituted lower alkyls, said R in each of formulae I and II being identical.

For purposes of the invention, the term "4 and 5" is used herein to designate a mixture of the 4- and 5-iodo isomers wherein the iodo atoms of the invention esters are in both an equatorial and axial conformation, thus providing a blend of four stereoisomers for each ester. The four stereoisomers are herein designated A$_1$, A$_2$, B$_1$ and B$_2$ as follows:

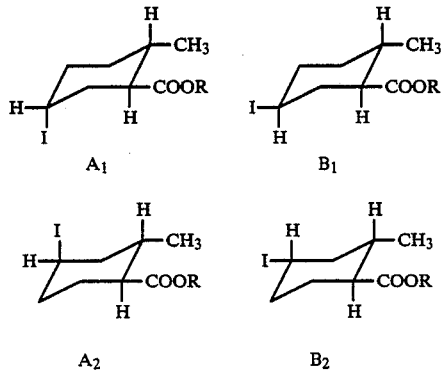

Examples of esters useful in the present invention are methyl 4(and 5)-iodo-trans-2-methylcyclohexanecarboxylate; ethyl 4(and 5)-iodo-trans-2-methylcyclohexanecarboxylate; propyl 4(and 5)-iodo-trans-2-methylcyclohexanecarboxylate; 1-methylpropyl 4(and 5)-iodo-trans-2-methylcyclohexanecarboxylate; 2,2,2-trifluoroethyl 4(and 5)-iodo-trans-2-methylcyclohexanecarboxylate; 1-methyl-2,2,2-trifluoroethyl 4(and 5)-iodo-trans-2-methylcyclohexanecarboxylate; 2,2,3,3,3-pentafluoro-1-methylpropyl 4(and 5)-iodo-trans-2-methylcyclohexanecarboxylate; and 2,2,3,3,4,4,4-heptafluoro-1-methylbutyl 4(and 5)-iodo-trans-2-methylcyclohexanecarboxylate.

Esters useful in the present invention maybe prepared as follows: The corresponding trans-6-methyl-3-cyclohexenecarboxylic acid (as prepared by a Diels-Alder reaction) is heated in a pressure vessel for 3 to 6 hours at elevated temperatures with aqueous hydriodic acid in the presence of an organic solvent, such as dioxane. The resultant iodo-trans-2-methylcyclohexanecarboxylic acid is a mixture of the 4- and 5-iodo isomers and is converted to the corresponding acid halide by reacting with a suitable halogenating agent, such as thionyl chloride, phosphorus trichloride or phosphorus tribromide, under mild conditions, preferably at room temperature. The acid halide is then reacted with the appropriate alcohol in a suitable solvent such as benzene or anhydrous ethyl ether in the presence of a hydrochloric acid scavenger, such as pyridine, to yield the ester.

Isolation of the ester is accomplished by sequentially washing the crude reaction mixture with dilute acid, dilute base and saturated salt solutions. The crude product is thereafter dried over a suitable drying agent, filtered and the solvent removed. Final purification is accomplished by fractional distillation under high vacuum. Individual stereoisomers of the esters can be separated by high-performance liquid chromotography.

The stereoisomeric content of the esters can be easily varied by changing the reaction temperature during preparation of the ester. For example, invention esters synthesized by the addition of hydrogen iodide to the Diels-Alder acid adduct at moderately elevated temperatures, i.e. from about 65° C. to 80° C., consist of a isomeric blend which has isomers $A_1$ and $A_2$ as its major components, with isomers $B_1$ and $B_2$ comprising about 10% to 20% of the blend. Esters synthesized by the addition of hydrogen iodide to the Diels-Alder acid adduct to about 95° C. to 130° C. consist of an isomeric blend which consists of greater than 50% of isomers $B_1$ and $B_2$. Consequently, the higher the temperature the greater the $B_1/B_2$ isomeric content in the resulting ester.

Of the four stereoisomers, the most attractive isomer is isomer $B_1$ having an equatorial iodo atom attached at the 5 carbon atom. For commercial practicalness, it is preferred to use a blend of isomers consisting predominantly of isomers $B_1$ and $B_2$. Preferably, the blend comprises an isomeric content of from about 50% to 100% of isomers $B_1$ and $B_2$ with isomers $A_1$ and $A_2$ comprising from about 0% to 50% of the blend.

The esters may be used as is or they may be dissolved in volatile inert solvents such as liquid hydrocarbons, emulsified in water, or admixed with any other solid or inert liquid carrier. When used in actual practice in the field, the compounds may be impregnated on a solid carrier such as paper, cloth, sawdust, wood chips, or other absorbent material. The attractants may also be dispersed into the atmosphere by spraying or by dipping wicks into containers holding the ester composition. Further, the attractants may be used in bait traps usually provided with means to prevent the exit of insects so that the size and location of infestations may be ascertained.

For optimum results, the esters of the invention should be used in a substantially pure form, that is, the ester must be free of undesirable contaminants that tend to mask or otherwise inhibit their effectiveness as an attractant. It is within the compass of the invention to use the esters either individually or in combination. The invention esters may also be used with other Medfly attractants of control agents, such as insecticides, chemosterilants or the like. When used, however, these agents should be used in an amount which, as readily determined by one skilled in the arts, will not interfere with the effectiveness of the invention esters.

Although the preparative procedures described above are the preferred synthesis for the compounds of the invention, it is within the scope of this invention to prepare the esters using any suitable hydriodic acid addition and esterification procedures.

The invention is further demonstrated by the following examples which are intended only to further illustrate the invention and not to limit the scope of the invention as defined by the claims.

EXAMPLE 1

The preparation of a blend of ethyl 4(and 5)-iodo-trans-2-methyl cyclohexanecarboxylate comprising more than 50% of isomers $B_1$ and $B_2$ using the Diels-Alder acid adduct intermediate is hereinafter illustrated.

21 g of trans-6-methyl-3-cyclohexenecarboxylate acid (0.15 mole) were added to a pressure bottle along with 60 ml of 57% hydriodic acid and 30 ml of p-dioxane. The pressure bottle was equipped with a magnetic stirrer, securely capped, and placed in an oil bath held at 115° to 125° C. The reaction mixture was stirred vigorously while being held in the bath for 3 hours. After cooling, the reaction mixture was poured into water and the organic layer was taken up in either. The ether layer was washed 2 times with water, then the organic acid was extracted from the crude reaction mixture with 10% aqueous sodium hydroxide. The alkaline portion was strongly acidified. The released organic acid was taken up in ether and was washed 3 times with water, then with dilute sodium bisulfite solution, again with water, dried over anhydrous magnesium sulfate and filtered. After removal of the solvent the crude iodo acid (ca 36 g) was used directly in the acid chloride synthesis. 26.8 g of the iodo acid (0.1 mole) was dissolved in 25 ml of benzene and 9 ml of thionyl chloride (0.125 mole) was added dropwise at room temperature. The reaction mixture was stirred overnight and the excess thionyl chloride and benzene were removed under vacuum with slight warming (40° C.). The crude acid chloride was added dropwise to an excess of ethanol (12 ml) and 8 ml of pyridine in anhydrous ether. After standing overnight, the reaction mixture was extracted sequentially with water, dilute aqueous hydrochloric acid and sodium hydroxide and finally with saturated salt solution. After drying over anhydrous magnesium sulfate, the crude product was isolated and purified by fractional distillation under high vacuum, b.p. 81° C./0.15 mm Hg, $n_D^{25}$ 1.5130, recovered yield 15.0 g, approximately 67% of which consisted of isomers $B_1$ and $B_2$ and 33% of isomers $A_1$ and $A_2$ (from gc peak height measurement). If the product darkens excessively after distillation, the excessive color can be removed by washing the product with dilute sodium bisulfite solution.

EXAMPLE 2

An isomeric blend of propyl 4(and 5)-iodo-trans-2-methylcyclohexanecarboxylate was synthesized in a 0.02 mole reaction in accordance with the procedure described in Example 1, and purified by distillation under high vacuum, b.p. 85° C./0.15 mm, $n_D^{25}$ 1.5065, recovered yield 2.67 g (about 67% isomers $B_1$ and $B_2$ and about 33% isomers $A_1$ and $A_2$ (from gc peak height measurement).

EXAMPLE 3

To determine the effectiveness of the blends of the invention a field test was conducted in a macadamia nut orchard at Keaau, Hawaii, in October 1987.

Medfly captures using isomeric blends of methyl, propyl, 1-methylethyl, 1-methyl-2,2,2-trifluoroethyl and 2,2,2-trifluoroethyl 4(and 5)-iodo-trans-2-methylcyclohexanecarboxylate were compared with those captures obtained by using TML. The ester blends used were (1) blends which consisted of about 100% $B_1$ and $B_2$ isomers; and/or (2) normal blends, that is, blends comprising isomers $A_1$, $A_2$, $B_1$ and $B_2$ wherein isomers $A_1$ and $A_2$ comprise more than 50% of the blend.

Treatments were applied to cotton wicks (9.5 mm diam. × 12.7 mm length; Johnson and Johnson No. 2) in standard Jackson sticky traps. Each attractant was applied in a 0.025 ml dosage undiluted to a wick. Six replicates were used. The TML wick was allowed to age along with the other attractants. Sterile laboratory-reared medflies were released throughout the test plot in a uniform manner at 0, 1, 2, 3, 4, 8, 10 and 13 days posttreatment. Fresh sticky inserts were placed in the traps prior to each release and remained in the trap throughout the test interval.

The TML used in the tests was obtained commercially from UOP in East Rutherford, N.J.

Data was analyzed by analysis of variance, and means were separated by Duncan's multiple range test at the P=0.05 level (Duncan 1951). The results are recorded in Table I.

Table I clearly shows the high attraction and superior persistence of ester blends comprising only isomers $B_1$ and $B_2$ over the normal blends. All of the $B_1B_2$ blends were significantly more attractive than their corresponding normal blends. In no case throughout the test did the catch of the normal mixture equal the catch obtained with the corresponding $B_1B_2$ blend. Of the ester blends tested, the $B_1B_2$ isomeric blend of the ethyl ester was the most attractive. Although not as initially attractive as the ethyl ester blend, the $B_1B_2$ isomeric blends of the propyl and the 1-methylethyl esters showed significant persistence over TML. After 2 days TML began to fail while the propyl and 1-methylethyl esters were effective up to 13 and 8 days, respectively. Further, the propyl and 1-methylethyl blends outlasted the ethyl ester up to 5 and 2 days, respectively.

EXAMPLE 4

The relative attractiveness of the four stereoisomers of ethyl 4(and 5-iodo-trans-2-methylcyclohexanecarboxylate, and mixtures thereof, were determined in a field test conducted in a macadamia nut orchard at Keaau, Hawaii, in February 1988.

Medfly captures obtained with fresh and aged TML was compared to captures obtained using the ethyl ester having the following isomeric content: (1) high $A_1$ and $A_2$, that is, more than 50% of isomers $A_1$ and $A_2$; (2) isomer $A_2$; (3) isomers $B_1$ and $B_2$; (4) isomer $B_1$ and (5) isomer $B_2$ with ca. 2.5% of isomer $B_1$.

The bioassay was the same as described in Example 4 except that a freshly baited TML wick was added to the test prior to each fly release and medflies were released at 0, 1, 3, 4, 8, 9, 10, 11 and 14 days posttreatment.

Data were analyzed in accordance with Example 4. The results are reported in Table II.

Table II shows that of the four stereoisomers of the ethyl ester, the most attractive isomer was the $B_1$ isomer. Traps with the $B_1$ isomer had higher mean catches than those of resh TML in the first 6 test periods and in 7 of the 9 test periods overall. Medfly captures with blends comprising the $B_1$ isomer were significantly as attractive as fresh TML up to 10 days. All isomeric mixtures of the ethyl ester tested were more persistent than aged TML which began to fail between days 1 and 3.

It is understood that modifications and variations may be made to the foregoing disclosure without departing from the spirit and scope of the invention.

TABLE I

Attraction of the Mediterranean Fruit Fly to Esters of 4(and 5)-Iodo-trans-2-methyl-cyclohexane-1-carboxylic Acid When Compared With Trimedlure (TML), October, 1987, Keaau, Hawaii

| Ester | Isomer blend[a] | Weighted mean catch/trap after indicated days of exposure in the field[b,c] | | | | | | | |
|---|---|---|---|---|---|---|---|---|---|
| | | 0 | 1 | 2 | 3 | 4 | 8 | 10 | 13 |
| TML-aged | | 162a | 176a | 122bc | 14f | 0f | 0e | 0d | 0c |
| Methyl | Normal | 5f | 5e | 6f | 9f | 7ef | 0e | 0d | 0c |
| | $B_1B_2$ | 31de | 38d | 45de | 49de | 48d | 0e | 0d | 0c |
| Ethyl | $B_1B_2$ | 157a | 216a | 190ab | 200a | 229a | 93b | 0d | 0c |
| Propyl | Normal | 33de | 62cd | 56de | 97bc | 91cd | 52c | 23b | 6b |
| | $B_1B_2$ | 69bc | 143ab | 122bc | 147ab | 165ab | 146a | 65a | 49a |
| 1-Methylethyl | Normal | 12ef | 36d | 49de | 58cde | 90cd | 19d | 7c | 0c |
| | $B_1B_2$ | 47cd | 84c | 94cd | 93bc | 125cd | 34cd | 8c | 0c |
| 1-Methyl-2,2,2-trifluoroethyl | Normal | 16ef | 39d | 33e | 29ef | 14e | 0e | 0d | 0c |
| | $B_1B_2$ | 49cd | 102bc | 52de | 64cd | 65d | 0e | 0d | 0c |
| 2,2,2-Trifluoroethyl | Normal | 107b | 197a | 207a | 167a | 144a | 0e | 0d | 0c |

[a]Normal blend is composed of 4 isomers, $A_1$, $A_2$, $B_1$, and $B_2$ wherein isomers $A_1$ and $A_2$ are more than 50% of the blend
[b]6 replicates; 0.025 ml dosage
[c]Catches followed by the same letter within a column are not significantly different (P > 0.05; Duncan's [1951] multiple range test).

TABLE II

Attraction Of The Mediterranean Fruit Fly To Varying Isomeric Blends of Ethyl 4(and 5)-iodo-trans-2-methylcyclohexanecarboxylate And To Its Individual Isomers $A_2$, $B_1$, AND $B_2$ When Compared With Trimedlure (TML).

| Isomer Content[a] | Weighted mean catch/trap after indicated days in the field[b] | | | | | | | | |
|---|---|---|---|---|---|---|---|---|---|
| | 0 | 1 | 3 | 4 | 8 | 9 | 10 | 11 | 14 |
| TML-(fresh) | 152a | 44ab | 63a | 92a | 136a | 130ab | 125a | 52b | 119a |
| TML-(aged) | 78bc | 19b | 10b | 0c | 0c | 0d | 0e | 0d | 0c |
| High $A_1A_2$[c] | 19de | 2c | 5b | 23b | 15b | 15c | 12d | 2cd | 3b |
| $A_2$ | 4e | 0c | 0c | 0c | 0c | 0d | 0e | 0d | 0c |
| High $B_1B_2$[c] | 113ab | 40ab | 50a | 109a | 96a | 91b | 41bc | 7c | 0c |
| $B_1B_2$ | 135ab | 60a | 65a | 123a | 126a | 109ab | 28cd | 6c | 0c |

TABLE II-continued

Attraction Of The Mediterranean Fruit Fly To Varying Isomeric Blends of Ethyl 4(and 5)-iodo-trans-2-methylcyclohexanecarboxylate And To Its Individual Isomers $A_2$, $B_1$, AND $B_2$ When Compared With Trimedlure (TML).

| Isomer Content[a] | Weighted mean catch/trap after indicated days in the field[b] | | | | | | | | |
|---|---|---|---|---|---|---|---|---|---|
| | 0 | 1 | 3 | 4 | 8 | 9 | 10 | 11 | 14 |
| $B_1$ | 172a | 63a | 73a | 121a | 139a | 144a | 103a | 85a | 116a |
| $B_2$[d] | 40cd | 3c | 8b | 22b | 15b | 12c | 1e | 0d | 0c |

[a]The 4 isomers that compose the trans blend are designated $A_1$, $A_2$, $B_1$ and $B_2$.
[b]Catches followed by the same letter within a column are not significantly different (P > 0.05; Duncan's [1951] multiple range test); 0.02 ml dosage; 6 replicates.
[c]High $A_1/A_2$ consists of isomers $A_1$, $A_2$, $B_1$ and $B_2$ wherein isomers $A_1$ and $A_2$ are more than 50% of the blend. High $B_1/B_2$ consists of isomers $A_1$, $A_2$, $B_1$ and $B_2$ wherein isomers $B_1$ and $B_2$ are more than 50% of the blend.
[d]Contained ca. 2.5% isomer B1.

We claim:

1. A composition to attract the Mediterranean Fruit Fly having, as an attractant, comprising an effective amount of a compound of the formula

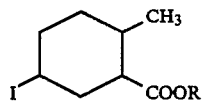

wherein —CH₃ and —COOR are in the trans-configuration and the iodo atom is equatorial, and wherein R is selected from the group consisting of ethyl, 2,2,2-trifluoroethyl, propyl, 1-methylethyl, and 1-methyl-2,2,2-trifluoroethyl, wherein said composition essentially is free of isomers of said compound having the iodo atom in the axial position.

2. The composition of claim 1 further including an inert carrier for said compound.

3. The composition of claim 1 further including a control agent for the Mediterranean Fruit Fly.

4. An composition to attract the Mediterranean Fruit Fly having, as an attractant, an effective amount of a mixture of compounds of the formulas

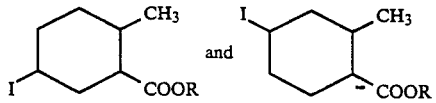

wherein —CH₃ and —COOR are in the trans-configuration and the iodo atom is equatorial, and wherein R is selected from the group consisting of ethyl, 2,2,2-trifluoroethyl, propyl, 1-methylethyl, and 1-methyl-2,2,2-trifluoroethyl, wherein said composition essentially is free of isomers of said compounds having the iodo atom in the axial position, said R in each of the formulas being identical.

5. The composition of claim 4 further including an inert carrier for said compounds.

6. The composition of claim 4 further including a control agent for the Mediterranean Fruit Fly.

7. A composition to attract the Mediterranean Fruit Fly having, as an attractant, an effective amount of a mixture of compounds of the formulas

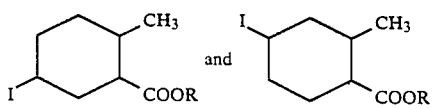

wherein —CH₃ and —COOR are in the trans-configuration and the iodo atom is equatorial and axial, but is more than 50% equatorial, and wherein R is selected from the group consisting of ethyl 2,2,2-trifluoroethyl, propyl, 1-methylethyl, and 1-methyl-2,2,2-trifluoroethyl, said R in each of the formulas being identical.

8. The composition of claim 7 wherein R is ethyl.

9. The composition of claim 7 wherein R is propyl.

10. The composition of claim 7 wherein R is 2,2,2-trifluoroethyl.

11. The composition of claim 7 further including an inert carrier for said compounds.

12. The composition of claim 7 further including a control agent for the Mediterranean Fruit Fly.

13. The composition of claim 12 where said control agent is an insecticide.

14. A method of attracting the Mediterranean Fruit Fly comprising subjecting said Fly for an extended period of time to a composition having, as an attractant, an effective amount of a compound of the formula

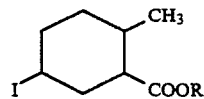

wherein —CH₃ and —COOR are in the trans-configuration and the iodo atom is equatorial, and wherein R is selected from the group consisting of ethyl, 2,2,2-trifluoroethyl, propyl, 1-methylethyl, and 1-methyl-2,2,2-trifluoroethyl, wherein said composition essentially is free of isomers of said compound having the iodo atom in the axial position.

15. A method of attracting the Mediterranean Fruit Fly comprising subjecting said Fly for an extended period of time to a composition having, as an attractant, an effective amount of a mixture of compounds of the formulas

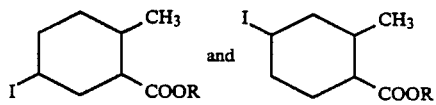

wherein —CH₃ and —COOR are in the trans-configuration and the iodo atom is equatorial, and wherein R is selected from the group consisting of ethyl, 2,2,2-trifluoroethyl, propyl, 1-methylethyl, and 1-methyl-2,2,2-trifluoroethyl, wherein said composition essentially is free of isomers of said compounds having the iodo atom in the axial position, said R in each of the formulas being identical.

16. A method of attracting the Mediterranean Fruit Fly comprising subjecting said Fly for an extended period of time to a composition having, as an attractant, an effective amount of a mixture of compounds of the formulas

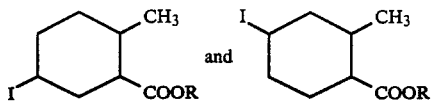

wherein —CH₃ and —COOR are in the trans-configuration and the iodo atom is equatorial and axial, but is more than 50% equatorial, and wherein R is selected from the group consisting of ethyl, 2,2,2-trifluoroethyl, propyl, 1-methylethyl, and 1-methyl-2,2,2-trifluoroethyl, said R in each of the formulas being identical.

17. The method of claim 16 wherein R is ethyl.
18. The method of claim 16 wherein R is propyl.
19. The method of claim 16 wherein R is 2,2,2-trifluoroethyl.
20. The method of claim 17 further including an inert carrier for said compounds.
21. The method of claim 17 further including a control agent for the Mediterranean Fruit Fly.
22. The method of claim 21 wherein said control agent is an insecticide.

* * * * *